United States Patent [19]

Marburg et al.

[11] Patent Number: 4,988,625

[45] Date of Patent: Jan. 29, 1991

[54] METHOD FOR DETERMINING THE FUNCTIONALIZATION OF A SOLID SUPPORT

[75] Inventors: Stephen Marburg, Metuchen; Richard L. Tolman, Warren, both of N.J.

[73] Assignee: Merck & Co., Inc., Rahway, N.J.

[21] Appl. No.: 269,221

[22] Filed: Nov. 9, 1988

[51] Int. Cl.$^5$ .................... G01N 31/00; G01N 33/00; G01N 30/02; G01N 33/44
[52] U.S. Cl. ........................................ 436/5; 436/111; 436/161; 436/85; 436/89
[58] Field of Search ..................... 436/111, 161, 85, 2, 436/5, 89, 183

[56] References Cited

U.S. PATENT DOCUMENTS 4,739,044 4/1988 Stabinsky .............................. 536/29
4,923,901 5/1990 Koester et al. ....................... 536/29

OTHER PUBLICATIONS

Scouten *Solid Phase Biochemistry*, 1983, pp. 36, 38, 39, 50.

Primary Examiner—Robert J. Warden
Assistant Examiner—Theresa A. Trembley
Attorney, Agent, or Firm—Richard S. Parr; Charles M. Caruso

[57] ABSTRACT

A solid support chemistry system which, with a dinitrofluorobenzene based assay, can be used to define titers of ligands and chemistry distal to the support. Cleavable diamine cystamines or 1,6-diamino-3,4-dihydroxyhexane are bonded to the solid support.

3 Claims, No Drawings

METHOD FOR DETERMINING THE FUNCTIONALIZATION OF A SOLID SUPPORT

BACKGROUND OF THE INVENTION

The use of solid supports in chemistry and affinity chromatography has received much attention in recent years. These methodologies involve the derivatization of a solid matrix and usually a subsequent chemical modification of the introduced functionalities. Since these solid matrices are generally insoluble in most solvents, evaluation of those transformations is problematic. Common questions in this regard involve quantitative concerns about titers of ligands and their long term stability on the support or qualitative questions regarding structural features of the ligands.

Some methods for evaluating transformed supports have been reviewed (Practical Guide For Use in Affinity Chromatography and Related TechniquesIBF/LKB pp. 43–45 (1983) and prominently include acid-base and redox titrations, microanalysis and indirect evaluation by difference. These methods are severely limited when the support is derivatized to a very small extent and generally do not afford structural information regarding the relevant ligand. This is so because the usual spectroscopic methods such as NMR do not work. Specific applications such as solid phase peptide and oligonucleotide synthesis are evaluated by cleavage of support-bound products followed by assays available to regular practitioners of these technologies. However, a generally applicable assay is not available since the chemistry involved in such an assay would have to be compatible with the large diversity of ligands and supports.

Cleavable bifunctional molecules are well known for their use in mapping contact sites of biomacromolecules (Pierce Handbook pp. 221–250, (1988) Pierce, Rockford, IL) and they have also been reported useful in affinity chromatography when elution of very tightly bound ligands is required (Jayabaskaran et al., *Preparative Biochem.*, 17, pp. 121–141 (1987); Mouton et al., *Biophys.*, 218, pp. 101–108 (1982); Singh et al., *Biophys.*, 218, pp. 284–293 (1979); Herman et al., *Anal. Biochem.*, 156, pp. 48–55 (1986), for purification of macromolecular reagents (Schwarzberg, U.S. Pat. No. 4,272,506 (1981), for reversible formation of synthetic vesicles (Chang et al., *Chem. Letters* pp. 1385–1388 (1987), and for reversible immobilization of enzymes (Carlson et al., *Hind.Antibiotic Bull.* 20, pp. 105–108 (1978)). The most common bond that is split in these linking) molecules is a disulfide moiety.

It is a purpose of the present invention to provide a solid support chemistry system which can be used to define titers of ligands using cleavable, bifunctional molecules.

It is also a purpose of the present invention to provide a solid support chemistry system which can be used to define chemistry distal to the support using cleavable, bifunctional molecules.

SUMMARY OF THE INVENTION

The present invention is a solid support chemistry system which, with a dinitrofluorobenzene based assay, can be used to define titers of ligands and chemistry distal to the support. The technology allows one to quantitatively monitor those parameters which are important to solid support chemistry. Ligand densities on several different types of support materials may be measured directly. Functional groups on these ligands may be determined and their chemical transformations evaluated.

The invention is based on the cleavability of bifunctional linking molecules. One of the functionalities of these bifunctional linking molecules is linked to the solid support, and the other functionality is available for binding to a ligand or bound to a ligand. When the functionality is available for binding to a ligand it is readily assayable.

The present invention is also a method for determining the level of functionalization of a solid support by
 (a) treating the solid support with carbonyl diimidazole to form a support capable of reacting with a cleavable, bifunctional linking molecule;
 (b) reacting the treated support with a cleavable, bifunctional linking molecule to form linker derivatized supports with stable carbamate bonds;
 (c) reacting the linker derivatized supports with a polysaccharide; and
 (d) determining the presence of pendant amino groups.

The present invention is also a method for chemically transforming a ligand by
 (a) attaching a first end of a cleavable, bifunctional linker molecule to a solid support;
 (b) attaching the ligand to a second end of the linker molecule;
 (c) chemically transforming the ligand; and
 (d) cleaving the cleavable, bifunctional molecule from the solid support.

The present invention is also a method for determining chemical events distal to a solid support having attached to it a cleavable, bifunctional linking molecule by
 (a) generating electrophilic sites by succinylating amino groups pendant to the support;
 (b) reacting the product of (a) with diisopropylcarbodiimide and p-nitrophenol to form a p-nitrophenyl ester;
 (c) reacting the ester with a nucleophile; and
 (d) monitoring the release of p-nitrophenolate.

Suitable solid supports are those which are inert to all reagents and solvents used in the present invention, and yet which may have attached to it one of the cleavable, bifunctional linking molecules described below. These include, but are not limited to, polysaccharide resins such as Sephadex or Sepharose, as well as polystyrene, polyamide and polyacrylamide resins.

Bifunctional molecules useful for the present invention include commercially available disulfide cystamines and novel 1,6-diamino-3,4-dihydroxyhexane.

Preferred disulfide cystamines are of the formula:

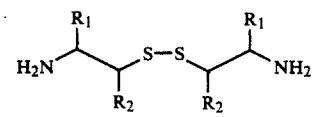

wherein $R_1$, is $CH_3$, $C_2H_5$ or $CO_2H$ and $R_2$ is hydrogen, $CH_3$ or $C_2H_5$.

Preferred disulfide cystamines are also of the formula:

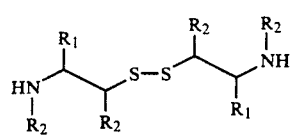

wherein $R_1$ is hydrogen, $CH_3$, $C_2H_5$ or $CO_2H$ and $R_2$ is hydrogen, $CH_3$ or $C_2H_5$, or wherein the $R_1$ and $R_2$ groups in combination form five or six membered rings, e.g.

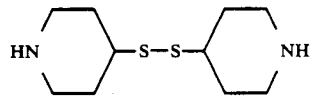

Disulfide cystamine bifunctional linking molecules are not preferred when reducing environments are necessary.

1,6-diamino-3,4-dihydroxyhexane, another preferred linking molecule, is shown below:

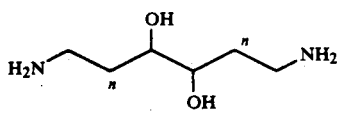

where n is 1. Compounds where n is 2 or 3 are also suitable for the present invention.

The cleavable, bifunctional linker molecules can be bonded to solid supports and used to define (a) titers of ligands and (b) chemistry distal to the support by employing an amine assay such as a dansyl, fluorescamine or dinitrofluorobenzene based assay. 1,6-diamino 3,4 dihydroxyhexane, which is cleavable with periodate, becomes a linking molecule which is stable to almost all conditions encountered in biochemistry and considerably hydrophilic in character. The disulfide amines, which are cleavable with dithiothreitol, can be applied to those systems which do not require reducing agents. The nucleophilic linking moieties are converted to cleavable electrophilic linkers by succinylation and p-nitrophenyl ester activation. The method allows the chemical definition of ligands containing amino groups which are prepared by deblocking protecting groups on the support.

DETAILED DESCRIPTION OF THE INVENTION

Preparation of cleavable, bifunctional 1,6-diamino-3,4 dihydroxyhexane may be carried out in the following manner. Commercially available 1,4-dicyano-2-butene, preferably purified, is converted to an epoxide. Preferred conversions, using high titer "70%" $H_2O_2$ and MgO, are capable of achieving conversions of up to 85%. The epoxide, which may be isolated by chromatography, is preferably hydrolyzed directly to 1,4-dicyano-2,3-dihydroxy butane to allow for purification from unreacted 1,4-dicyano 2 butene by simple extraction. A preferred two step synthesis involves hydrogenation and conversion to a friable dihydrochloride. 1,4-dicyano-2,3 dihydroxy butane is found to be in the erythro configuration by single crystal X-ray determination, implying the same configuration as 1,6-diamino-3,4 dihydroxyhexane.

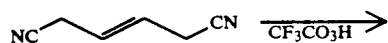

1,4-dicyano-2-butene

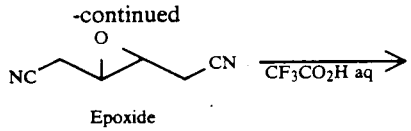

Epoxide

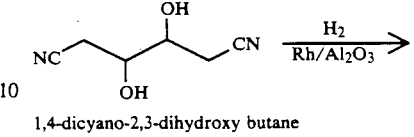

1,4-dicyano-2,3-dihydroxy butane

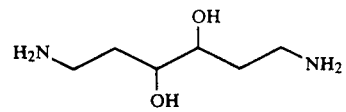

1,6-diamino-3,4-dihydroxyhexane

The following examples are illustrative of procedures for making and using cleavable, bifunctional linker molecules useful in the present invention, and should not be read as limiting the scope of the invention.

EXAMPLE I

Preparation of 1,6-diamino 3,4 dihydroxyhexane

A. Preparation of 1,4-dicyano 2,3-dihydroxy butane 1,4-dicyano 2-butene (25 g) (Aldrich) dissolved in 200 mL of $CH_2Cl_2$ was filtered through Celite and stripped to dryness in vacuo. The material (24 g) was then recrystallized from 50 mL of isopropanol (IPA) affording 22 g of 1,4 dicyano 2-butene crystals after drying (mp 75°-76° C.). To a 500 mL round bottom flask containing 100 mL of methylene chloride ($CH_2Cl_2$) and cooled in an ice acetone bath to $-5°$ C. was added 5.4 mL of 70% $H_2O_2$. Trifluoroacetic anhydride, 26 mL (28.7 g/0.18 mol) was then added dropwise at a rate which maintained a temperature of 0° C. After completion of the addition, the mixture was stirred at $-5°$ C. for 0.5 h and then 3.5 g of powdered MgO was added. The ice bath was removed, the mixture was warmed to room temperature (r.t.) and then 10.3 g (0.097 moles) of 1,4-dicyano2-butene in 100 mL of $CH_2Cl_2$ was added dropwise over a period of an hour. The reaction mixture was periodically cooled to maintain a maximum temperature of 35° C. After completion of the addition, the mixture was aged at r.t. for 48 h at which time the HNMR spectrum showed an 85% conversion to the epoxide. Because of the sensitive nature of the reaction, it is appropriate to monitor its extent by NMR. The gel which is formed is then dissolved by washing with 2×50 mL of $H_2O$ and the aqueous layers back washed with 100 mL of $CH_2Cl_2$. The combined $CH_2Cl_2$ layers are stirred for 2 h at r.t. with 1.0 g of 10% Pd on carbon, filtered through Celite (no starch-iodide color afforded) and concentrated to 10 g of an oil in vacuo. This was heated at reflux in 300 mL of 10% aqueous trifluoroacetic acid for 1.5 h, cooled and extracted with 3×50% mL of $CH_2Cl_2$. After decolorizing the aqueous layer (2.5 g Darco G 60/0.5 h), the Celite filtered solution was concentrated in vacuo to about 14 g of an oil. This was crystallized from 80 mL of butyl acetate affording 5.5 g of 1,4-dicyano-2,3-dihydroxy butane mp 94°-96° C. (yield 43%). Calcd for $C_6H_8N_2O_2$: C, 51.47; H, 5.57; N, 19.99. Found: C, 51.29; H, 5.77; N, 19.86. 200 MHz NMR ($D_2O$): (AA'BB'XX' system) 2.86 ppm (m, 4H); 3.91 (m, 2H).

B. Preparation of 1,6 diamino-3,4-dihydroxyhexane dihydrochloride

A hydrogenation bomb was charged with 4.0 g (0.029 mol) 1,4-dicyano-2,3-dihydroxybutane dissolved in 320 mL of 1:1 isopropanol/trifluoroacetic acid. This solution was hydrogenated under 1000 psi $H_2$ at r.t. in the presence of 1.2 g 5% Rh on alumina for 24 h. To the reaction mixture was then added 100 mL of $H_2O$ which formed a second layer. Both layers were then filtered through Celite. The organic layer (lower) was then washed $2 \times 50$ mL of $H_2O$ and all the aqueous fractions combined and stripped to constant weight (11 g) in vacuo. The solid was then dissolved in 40 mL of 6N HCl and concentrated to dryness in vacuo. This step was repeated two times. The crude dihydrochloride (5.89 g) was recrystallized from 130 mL of 2:2:1 DMF/acetonitrile/$H_2O$ affording 3.89 g of 1,6-diamino-3,4-dihydroxyhexane dihydrochloride, yield 66%. Calcd for $C_6H_{18}Cl_2N_2O_2$: C, 32.59; H, 8.20; N, 12.67; Cl, 32.07. Found: C, 32.66; H, 7.98; N, 12.51; Cl, 32.30. 200 MHz NMR ($D_2O$): 1.79 (m, 2H); 1.98 (m, 2H); 3.18 (m, 4H); 3.67 (m,2H).

C. Preparation of N,N'-bis-(2,4-dinitrophenyl)-1,6 -diamino-3,4-dihydroxy hexane A 25 mL round bottom flask fitted with a magnetic stirrer was charged with 221.1 mg (1.0 mmol) of 1,6 diamino-3,4-dihydrox-yhexane dihydrochloride, 409 mg (2.2 mmol) of 2,4-dinitrofluorobenzene, 130 mg (0.94 mmol) of $K_2CO_3$ and 10 mL of $H_2O$. The mixture was stirred at 75° C. for 5 h. After cooling the yellow precipitate was isolated by filtration, washed with $H_2O$ and dried, affording 310 mg of crude product. This material (46 mg) was recrystallized from 2 mL of 1:1 $H_2O$/DMF affording 20.4 mg of N,N'-bis(2,4-dinitrophenyl)-1,6 diamino-3,4-dihydroxy-hexane, mp 199° C. dec. Calcd for $C_{18}H_{20}N_6O_{10}$: C, 45.00; H, 4.17; N, 1750. Found: C, 44.68; H, 4.19; N, 17.12. 200 MHz NMR (acetone-$d_6$): 1.9 (m, 2H), 2.15 (m, 2H), 3.78 (m, 6H); 4.34 (d, J =4.8 Hz, 2H, active H), 7.30 (d, J=9.6, 2H), 8.30 (dd, J =2.2, 9.6, 2H), 8.99 (d, J=2.6 Hz, 2H), 9.1 (m, 1H).

with 10 mL of $CH_2Cl_2$. The yellow crystals were washed with additional $CH_2Cl_2$ and recrystallized from 0.5 mL of 15:85 $H_2O$/DMF. The isolated product was washed with 1:1 $H_2O$/DMF affording 77 mg of N,N'-bis-(2,4-dinitrophenyl) cystamine, mp 175°–176° C. Calcd for $C_{16}H_{16}N_6O_8S_2$: C, 39.67; H, 3.31; N, 17.36; S, 13.22. Found: C, 39.74; H, 3.38; N, 17.26; S, 13.48. 200 MHz NMR (DMSO-$d_6$): 3.08 (t, J =6.6, 4H), 3.80 (4 lines, 4H), 7.27 (d, J =9.6, 2H), 8.25 (dd, J =2.8, 9.6, 2H), 8.84 (dd, J =2.8, 0.8, 2H), 8.93 (t, J=5.6, 2H).

The cleavable functional linkers are useful for evaluating the combining potential of commercially available solid supports such as Sepharose CL-6B which are activated in an electrophilic sense. Their combining titers frequently diminish with time, causing uncertainty as to the true value of the combining potential. In the same sense it is useful to know what level of functionalization is obtained with a given activation protocol when an unactivated support is used as a starting material. In conflict with the assumption that the presence of a diamino ligand (e.g. 1,6 hexane diamine), often determined by elemental analysis, reflects the availability of the relevant nucleophilic amino group, we found large discrepancies between the information obtained using elemental analysis and the information obtained using amine titer (DNFB method). As shown in Table I, the level of ligand determined by elemental analysis is consistently higher than the amine titer, a result which can be explained by a reaction of the distal amino function which forms a non basic center, such as a carbamate. We have also found, in contrast with what is known in the art, that time dependent changes occur with resins after the support has been functionalized. Depending on the type of treatment of the carbonyl diimidazole activated Sepharose CL-6B after reaction with 1,6 diamino 3,4 dihydroxyhexane, the resin showed different time-dependent changes of titers. An acid washing of the resin rapidly afforded a stable titer and water washing was similar except that more scatter was observed in the assays. However when the resin was "capped" with ethanolamine, a time dependent monotonic decrease of amine titer resulted and the supernatant gradually became positive in the ninhydrin assay.

TABLE I

Characteristics of Cleavable Linker Functionalized Supports

| Resin | Ligand | $NH_2$ Titer[a] µmole/mL resin | Ligand[b] loading µmole/µL resin | Dry Weight of 100 mL Aliquot (mg) |
|---|---|---|---|---|
| A: Sepharose CL-6B | cys | 25 ± 3.5 (n = 22) | 41 ± 6 | 5.0 ± 0.26 (n = 7) |
| B: Sepharose CL-6B | DHL | 32.8 ± 1.7 (n = 4)[c] | 32.1 ± 4.6 | 4.3 ± 0.26 (n = 5) |
| C: Trisacryl GF2000 | cys | 16.4 ± 1.5 (n = 9) | 22.6 ± 8.3 | 17.6 ± 1.1 (n = 7) |
| D: Trisacryl GF2000 | DHL | 31.6 ± 0.5 (n = 4)[c] | — | 18.6 ± 1.3 (n = 5) |
| E: Activated CH Sepharose 4B | DHL | 10.3 ± 0.5 (n = 3) | — | — |

[a]average value ± std. dev. (no. of determinations) by DNFB method
[b]average incorporation determined by elemental anaylsis (S and/or N); deviation calulated on basis of 0.3 allowable error in analysis
[c]acid washed product; values depend on nature of preparation

EXAMPLE II

Preparation of N,N'-bis (2,4-dinitrophenyl)cystamine

A 25 mL round-bottom flask fitted with a magnetic stirrer was charged with 225 mg (1.0 mmol) of cystamine dihydrochloride, 409 mg (2.2 mmol) 2,4-dinitrofluorobenzene, 25 mg of $K_2CO_3$, and 10 mL of $H_2O$. The mixture then stirred in a 75° C. oil bath for 18 h. After cooling, the solvent was decanted from a yellow insoluble sludge. The sludge crystallized on trituration Another application of this technology is the evaluation of chemical events distal to the support and cleavable linker. These transformations and how they may be evaluated at each step are outlined below. We have generated electrophilic sites by succinylating the pendant amino groups of I to yield II and activating the product by forming a p-nitrophenyl ester, III. The p-nitrophenyl ester may then be reacted with amines and other nucleophiles, and released p-nitrophenolate can be used to monitor the reaction.

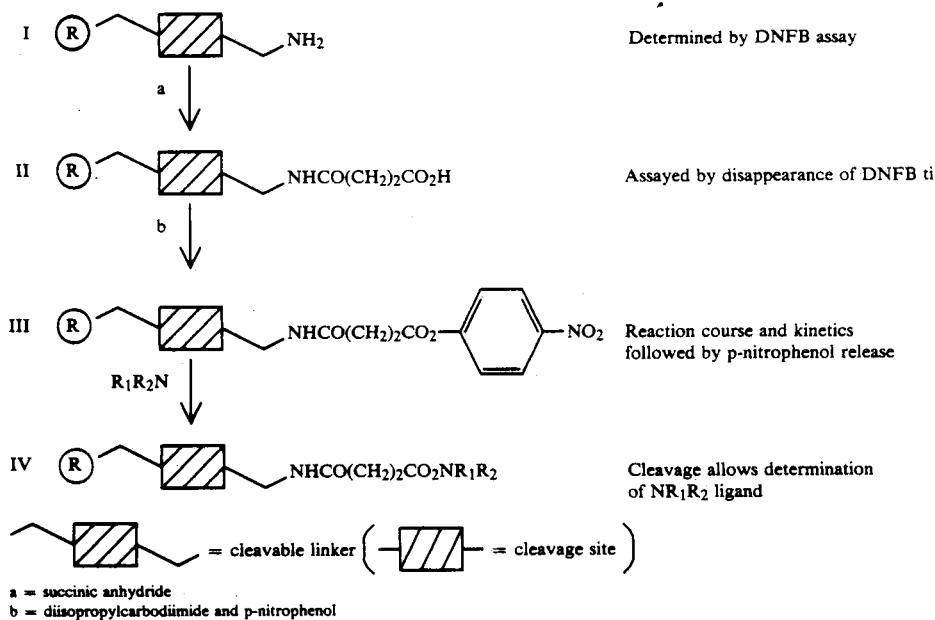

Determined by DNFB assay

Assayed by disappearance of DNFB ti

Reaction course and kinetics followed by p-nitrophenol release

Cleavage allows determination of $NR_1R_2$ ligand a = succinic anhydride
b = diisopropylcarbodiimide and p-nitrophenol
Ⓡ = resin (e.g. Sepharose CL-6B)

Coupling polysaccharides to solid supports involves the reaction of an amino functionalized polysaccharide with a electrophilic support. Specifically, we coupled the butane diamine derivative of the *H. infuenzae* b polysaccharide (PRP-BuA$_2$; Marburg et al., (1986) (*J.Am. Chem. Soc.*, 108, 5282–5287) to an electrophilic resin having a cystamine linker. This allowed a mild cleavage of the product by DTT, releasing the polysaccharide into the solution where it could be assayed. Normally such an evaluation would be difficult since PRP has no distinct chromophore and a carbohydrate-based support such as Sepharose would severely complicate release by drastic hydrolysis. The present invention therefore enables one to chemically define polysaccharide-support conjugates.

Electrophilic solid supports useful in the present invention are preferably prepared by reaction with carbonyl diimidazole according to the procedure described by Bethell et al., (1979) *J. Biol. Chem.*, 254, 2572–2574. The supports may then be coupled to disulfide cystamine or 1,6-diamino-3,4-dihydroxyhexane cleavable, bifunctional linking molecules, forming linker derivatized supports with stable carbamate bonds.

A sampling procedure for solid resins was developed using Wiretrol disposable pipets which had an approximate 6% variability (Table I). This was determined by drying 100 μL aliquots in vacuo and determining their weights. Completion of the dinitrophenylation and cleavage reactions were determined by repeating these operations on a given sample and finding no increases in the amine titers.

If there is a pendant amine on the support, the resin becomes bright yellow after dinitrophenylation and then colorless after cleavage. In cases of complex chemistry involving non-cleavable amines in addition to cleavable linkers, the resin can turn yellow on dinitrophenylation but the color is not released on cleavage.

Results of the assay are shown in Table I and include values determined when the support had not reached its final titer. Therefore deviations, which are in the range of 15%, are maximal and we believe that with a stable resin the analysis has no more than 10% variability.

The 1,6-diamino-3,4-dihydroxyhexane linker can be effectively cleaved when larger molecular moieties are appended to it. As can be seen by the double cleavage experiment outlined below, both cleavage products of the dinitrophenylated cystamine adduct of III afford the same titer.

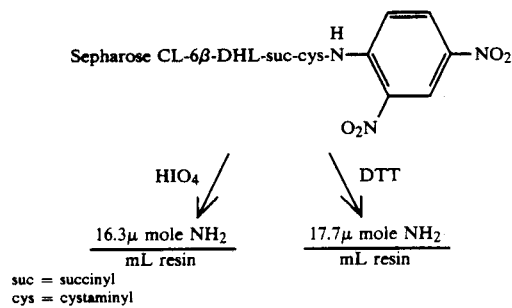

suc = succinyl
cys = cystaminyl

This methodology also enables one to evaluate free amino groups which have been generated by deprotection of a ligand which has been bound to a support. Using nucleophilic-electrophilic chemistry, direct introduction of a ligand which bears a free amino functionality is problematical since electrophilic resins bind amino groups and electrophilic ligands require protected amino functionalities. An important consideration for the solution involving masked amino groups is evaluation of the deprotection. Several resins were prepared which necessitated a free piperazine 4′-amino group. Piperazine itself couples to an electrophilic resin and its identification by the DFNB method is evidenced by a wavelength shift indicative of a secondary amine. 4′-BOC-piperazine (Carpino et al., (1983) (*J.Org.Chem.*, 48, 661–665) releases p-nitrophenol from the resin but affords no DNFB titer. The BOC group can be removed in 0.1N HCl, the kinetics (t½ ~ 17h) and the final titer can be monitored by the DNFB method and the structure supported by the bathochromic wavelength shift. The method was successfully applied to ligands having 4'-BOC-peperazinyl moieties activated as p-nitrophenyl esters. They were bound to DHL-Sepharose CL-6B.

EXAMPLE III

Assay of Pendant Amino Groups on Functionalized Solid Supports (DNFB Method)

The method described below was used to evaluate pendant amino groups on functionalized solid supports. The assay may be used when either the 1,6-diamino-3,4-dihydroxyhexane or a diamine cystamine cleavable, bifunctional linking molecule is used.

A 100 μL aliquot of the derivatized solid support is sampled by drawing up an excess in a 100 μL Wiretrol disposable syringe (Drummond Scientific Co., Broomall, PA 19008) and allowing it to settle in an inverted position to constant volume (ca 10 min). The plunger is set for 100 μL and the resin is delivered to a 15 mL centrifuge tube. It is then covered with 2.0 mL of ethanol, 40 μL of 2,4-dinitrofluorobenzene and 20 μL of N,N-diisopropylethylamine added and the mixture heated with occasional shaking for 15 min in a 75° C. bath. The resin is then centrifuged, the yellow ethanol supernatant removed and the resin washed with (1) 10 mL of ethanol, (2) 10 mL of 1:1 ethanol: $H_2O$ and (3) 10 mL of $H_2O$. At this point there is no color or U.V. absorption in the supernatant, but the resin is bright yellow if amino groups are present. In the case of a cystamine linker, the chromophore is cleaved by (a) adding 5.0 mL of a 0.1 M pH 11 sodium borate buffer and 51±3 mg of dithiothreitol (DTT) and (b) agitating on an Adams Nutator (Fisher & Co.) for 15 min. After centrifugation, 2 mL of the supernatant is diluted to 25 mL with 0.1 N HCl and the O.D. read at 361 nm. Other appropriate dilutions are made when linker density warrants. The titer of pendant amine is computed from: O.D./$1.6\times10^4\times624\times10^5$ = μmole $NH_2$/ml resin. When 1,6 diamino-3,4 dihydroxyhexane is the linker, cleavage is accomplished by covering the washed, dinitrophenylated resin with 5.0 mL of $HIO_4$ (aq) (10mg/mL), agitating for 15 min, diluting 2.0 mL of the supernatant to 25 mL with 0.1N HCl and reading the O.D. at 361 nm. Once again, linker density may warrant further dilution. Calculation is according to $O.D./1.5\times10^4\times625\times10^5$ = μm $NH_2$mL resin. When a secondary amine such as piperazine is the amine in question, an $\epsilon = 1.37\times10^4$, determined at 392 nm, was used in the calculation.

EXAMPLE IV

Preparation of H. influenzae type b Polysaccharide Sepharose CL-6B Conjugate

Preparation of DHL-sepharose:

Sepharose CL-6B (20 mL) was sequentially washed with 300 mL each of $H_2O$, 3:7 dioxane:$H_2O$, 7:3 dioxane:$H_2O$ and then tumbled with 120 mL of dry dioxane for 0.5 h. The resin was then filtered and covered with 30 mL of fresh dioxane 750 mg of carbonyl diimidazole was added (CDI) and the mixture tumbled for 3 h. The resin was then filtered, washed with 270 mL of dioxane, returned to a 50 mL centrifuge tube and reacted with an aqueous solution of 1,6-diamino-3,4-dihydroxyhexane (30 ml, 0.1 g of the dihydrochloride/mL), the pH of which had been adjusted to 9.96. After tumbling the resin at 4° C. for 18 h, the resin was washed on a filter with $H_2O$ (400 mL), 1M aqueous NaCl (200 mL and $H_2O$ (1 L). The final washings were negative in a ninhydrin test and the resin assayed for 33.9 μmoles $NH_2$/mL resin (DNFB).

Succinylation of DHL-Sepharose

To 3 mL of DHL-sepharose covered with 7 mL of pH 11 0.1M borate buffer was added 135 mg of succinic anhydride, and the mixture tumbled for 2 h at r.t. After removal of the aqueous supernatant, the resin was again covered with the same reagents and tumbled for 16 h, affording the succinylated DHL-sepharose, 0.0 μmoles $NH_2$/mL resin (DFNB).

Preparation of the p-nitrophenyl ester of the succinylated DHL-sepharose 1.3 mL of the succinylated resin was covered with 3.5 mL of 0.1N HCl, tumbled for 20 min and then washed with 3:1 DMF:$H_2O$ followed by 4 mL of DMF. The resin was then covered with 1 mL of fresh DMF and tumbled for 16 h at r.t. with 65 mg of p-nitrophenol and 0.120 mL of diisopropylcarbodiimide. Removal of the supernatant followed by washing with 30 mL of isopropanol afforded the p nitrophenyl ester which was stored in 0.01N HCl at 4° C.

Reaction of the p nitrophenyl ester with cystamine

The pH of a cystamine hydrochloride solution (419 mg/ 10 mL pH 8 phosphate buffer) was adjusted to pH 8 and then added to the p nitrophenyl ester from above. After tumbling for 2 h at r.t., the resin was washed with $H_2O$ until neither the supernatant nor the resin turned yellow with 2N $NH_3$ and the supernatant was negative in a ninhydrin test.

Double Cleavage

The resin was now dinitrophenylated and washed as usual and two 100 μl aliquots were removed. One was cleaved using the DTT protocol affording a titer of 17.7 μmoles/mL of resin and the other was cleaved using the $HIO_4$ protocol a titer of 16.3.

Preparation of a Piperazine Linked Sepharose

To 1.5 mL of a succinylated DHL Sepharose CL-6B p-nitrophenyl ester (vide supra) was added 1.0 g of 4-BOC piperazine (Carpino et al., (1983) *J. Org. Chem.*, 48, 661–665) in a pH 7.3 phosphate buffer. The reaction mixture was tumbled overnight, washed thoroughly with $H_2O$ (negative ninhydrin and no yellow color with 2N $NH_4OH$) and then assayed (DNFB). A zero amine titer was observed. The resin was covered with 10mL of 0.1N HCl and tumbled at r.t., aliquots removed, washed and assayed at various times. After 270 h, a limiting titer of 13.6 μM NH/mL resin ($\lambda_{max}=380$ nm) was found indicating deblocked piperazine.

Preparation of the Conjugate

The p-nitrophenyl ester of succinylated cystamine functionalized Sepharose CL-6B (cys-Sepharose) was prepared in the same manner as the DHL-Sepharose CL-6B analog (vide supra) and to 3.5 mL of this resin was added a solution of 126 mg of PRP-$BuA_2$ (Marburg et al., 1986) in 4 mL of 0.1M phosphate buffer with the pH adjusted to 8.5. The mixture was tumbled for 92 h at r.t. (final pH = 8.01). The supernatant was then removed and the resin washed by centrifugation with $2\times40$ mL of $H_2O$, $2\times40$ mL of phosphate buffered saline (PBS) at pH 7.2 and 40 mL of H₂O. A final 10 mL H₂O wash was analyzed for ribose by the method of Dische and Schwarz (Dische et al., (1937) *Mikrochim. Acta*,2, 13–19) and none was found. The resin (0.7 mL) was then covered with 5 mL of 0.1M borate buffer (pH 11) and tumbled with 57 mg of DTT for 1.5 h. This released 53 μgrams of PRP (by ribose assay) into the supernatant which is equivalent to 0.38 mg/mL resin.

Other polysaccharide protein conjugates may be prepared using the techniques of the present invention.

Polysaccharides which are useful for this invention are any bacterial polysaccharides with acid groups, but are not intended to be limited to any particular types. Examples of such bacterial polysaccharides include *Streptococcus pneumoniae* (pneumococcal) types 6A, 6B, 10A, 11A, 18C, 19A, 19F, 20, 22F, and 23F polysaccharides; Group B Streptococcus types Ia, Ib, II and III; *Haemophilus influenzae* (H. flu) type b polysaccharide; *Neisseria meningitidis* (meningococcal) groups A, B, C, X, Y, W135 and 29E polysaccharides; and *Escherichia coli* K1, K12, K13, K92 and K100 polysaccharides. Particularly preferred polysaccharides, however, are those capsular polysaccharides selected from the group consisting of H. flu type b polysaccharide, such as decribed in Rosenberg et al, *J. Biol. Chem.*, 236, 2845–2849 (1961) and Zamenhof et al., *J. Biol. Chem.*, 203, 695–704 (1953); *Streptococcus pneumoniae* (pneumococcal) type 6B or type 6A polysaccharide, such as described in Robbins et al., *Infection and Immunity*, 26, No. 3, 1116–1122 (Dec., 1979); pneumococcal type 19F polysaccharide, such as described in C.J. Lee et al., *Reviews of Infectious Diseases*, 3, No. 2, 323–331 (1981); and pneumoccocal type 23F polysaccharide, such as described in O. Larm et al., *Adv. Carbohyd. Chem. and Biochem.*, 33, 295–321, R. S. Tipson et al., ed., Academic Press, 1976.

Proteins which are useful for this invention are those of proven safety and demonstrable immunogenicity, but are not limited to any particular type. Suitable proteins include bacterial membrane proteins; any of various plant proteins, such as edestin or soybean trypsin inhibitor; viral protein subunits, such as hepatitis A or B, herpes gD or gC, Epstein-Barr or varicella zoster subunits; synthetic polypeptides; diphtheria toxoid; or tetanus toxoid, but are preferably *Neisseria meningitidis* (meningococcal) B serotype outer membrane proteins, which are T-cell stimulators. An example of these serotype proteins has been described in Helting et al., "Serotype Determinant Proteins of *Neisseria Meningitidis*", Actapath. Microbiol. Scand. Sect. C, 89, 69–78 (1981), and Frasch et al., *J. Bact.* 127, 973–981 (1976).

What is claimed is:

1. A method for determining the level of functionalization of a solid support comprising
   (a) treating the solid support with carbonyl diimidazole to form a support capable of reacting with a cleavable, bifunctional linking molecule;
   (b) reacting the treated support with a cleavable, bifunctional linking molecule to form linker derivatized supports with stable carbamate bonds;
   (c) reacting the linker derivatized supports with a polysaccharide; and
   (d) determining the presence of pendant amino groups so as to provide an indication of the functionalization of a solid support.

2. A method of claim 1 wherein the cleavable, bifunctional linking molecule is 1,6-diamino 3,4-dihydroxyhexane.

3. A method of claim 1 wherein the cleavable, bifunctional linking molecule is a disulfide cystamine.

* * * * *